United States Patent
Maxson et al.

(10) Patent No.: US 8,475,531 B1
(45) Date of Patent: Jul. 2, 2013

(54) ANCHORED MULTI-PHASIC OSTEOCHONDRAL CONSTRUCT

(76) Inventors: Scott A. Maxson, Central, SC (US); Karen J. L. Burg, Clemson, SC (US)

(*) Notice: Subject to any disclaimer, the term of this patent is extended or adjusted under 35 U.S.C. 154(b) by 238 days.

(21) Appl. No.: 12/763,515

(22) Filed: Apr. 20, 2010

Related U.S. Application Data

(60) Provisional application No. 61/171,215, filed on Apr. 21, 2009.

(51) Int. Cl.
*A61F 2/08* (2006.01)
*A61F 2/28* (2006.01)

(52) U.S. Cl.
USPC ............. 623/14.12; 623/23.5; 623/23.51; 623/23.58; 623/23.61

(58) Field of Classification Search
USPC .......................... 623/23.51, 23.56
See application file for complete search history.

(56) References Cited

U.S. PATENT DOCUMENTS

| | | | |
|---|---|---|---|
| 5,200,248 A | 4/1993 | Thompson et al. | |
| 5,554,194 A | 9/1996 | Sanders | |
| 5,626,861 A | 5/1997 | Laurencin et al. | |
| 5,705,118 A | 1/1998 | Hayes et al. | |
| 5,866,155 A | 2/1999 | Laurencin et al. | |
| 5,972,505 A | 10/1999 | Phillips et al. | |
| 6,417,247 B1 | 7/2002 | Armstrong et al. | |
| 6,454,811 B1 | 9/2002 | Sherwood et al. | |
| 6,626,950 B2* | 9/2003 | Brown et al. | 623/23.72 |
| 7,026,014 B2 | 4/2006 | Luzinov et al. | |
| 7,319,035 B2 | 1/2008 | Vacanti et al. | |
| 7,361,195 B2 | 4/2008 | Schwartz et al. | |
| 2003/0114936 A1 | 6/2003 | Sherwood et al. | |
| 2004/0002770 A1* | 1/2004 | King et al. | 623/23.51 |
| 2006/0036331 A1* | 2/2006 | Lu et al. | 623/23.51 |
| 2007/0113951 A1 | 5/2007 | Huang | |

OTHER PUBLICATIONS

Devin, et al., "Three-dimensional degradable porous polymer-ceramic matrices for use in bone repair", *J. Biomater. Sci. Polymer Edn.*, vol. 7, No. 8, pp. 661-669 (1996).
Abstract—Mikos, et al., "Preparation and Characterization of poly(L-lactic acid) foams", *Polymer*, vol. 35, Issue 5, pp. 1068-1077 (Mar. 1994).
Schwartz, et al., "Calvarial bone repair with porous D.L-polylactide", *Otolaryngology-Head and Neck Surgery, Journal*, vol. 112; Issue 6, pp. 707-713 (Jun. 1995).
Thomson, et al., "Fabrication of biodegradable polymer scaffolds to engineer trabecular bone", *J. Biomater. Sci. Polymer Edn*, Vol, 7, No. 1, pp. 23-28 (1995).

* cited by examiner

*Primary Examiner* — Thomas J Sweet
*Assistant Examiner* — Brian Dukert
(74) *Attorney, Agent, or Firm* — Dority & Manning PA

(57) ABSTRACT

Disclosed are osteochondral constructs that can be utilized to encourage both bone and articular cartilage tissue repair in synovial joints. Disclosed constructs are composites including a hydrogel portion for implant in a cartilage defect site and an adjacent portion for implant in a bone defect site. The portion to be implanted in a bone defect site can include a polymeric/ceramic composite material. Disclosed constructs also include a polymeric anchor that can secure the construct at the desired site. Disclosed constructs can also include capillary channeled fibers within the bone portion of the construct that can provide improved nutrient flow to and waste flow from cells growing and developing on and in the construct.

15 Claims, 8 Drawing Sheets

US 8,475,531 B1

ANCHORED MULTI-PHASIC OSTEOCHONDRAL CONSTRUCT

CROSS REFERENCE TO RELATED APPLICATION

The present application claims filing benefit of U.S. Provisional Patent Application having Ser. No. 61/171,215 with a filing date of Apr. 21, 2009, which is incorporated herein by reference in its entirety.

BACKGROUND

Synovial joints (diarthroses, diarthroidal joints) are the most common joints in the human body providing the greatest range of motion. Synovial joints include a capsule surrounding the articulating bone surfaces. The capsule is formed with a synovial membrane that excretes synovial fluid into the joint space and hyaline cartilage that lines the articulating ends of the joint bones and lies within the fluid-filled capsule.

One of the most frequent causes of physical disability among adults is osteoarthritis, which affects the articular cartilage as well as adjacent tissues of synovial joints. Damage to the articular cartilage due to traumatic injury, disease, or the natural aging process can lead to osteoarthritis. Symptoms of mild osteoarthritis can include joint pain, stiffness, and loss of mobility, while severe cases can include gross joint deformity and bony overgrowth, complete cartilage loss and collapse of the underlying subchondral bone.

Cartilage is an avascular tissue including between about 5 and 10% by weight chondrocytes. Chondrocytes have limited mobility as well as limited ability to divide and regenerate damaged tissue. Thus, damage to the articular cartilage is not accessed by blood, macrophages, or mesenchymal stem cells, and exhibits poor healing. Osteochondral damage that extends through the full thickness of the cartilage and encompasses damage to the subchondral bone will be accessed by blood and mesenchymal stem cells, but this in turn can lead to neovascularization and ingrowth of fibrocartilage to the cartilage layer, rather than regrowth of healthy cartilage. Moreover, osteochondral defects can often lead to an ingrowth of osteocytes in the cartilage area, followed by calcium deposition and new bone growth, leading to further deformation of the joint.

Attempts have been made to develop treatment methods that can address the unique requirements of the two different, adjacent tissue types so as to encourage proper healing of both the articular cartilage and, where necessary, the subchondral bone. For instance, U.S. Pat. No. 6,626,950 to Brown, et al. discloses a prosthetic implant including an anchoring post embedded within a tissue scaffold, the tissue scaffold including a porous ceramic phase, a porous polymer phase, and an interphase between the two. U.S. Pat. No. 7,361,195 to Schwartz, et al. discloses an orthopedic device including a plug to be positioned in hole formed in damaged cartilage and an anchor configured to support the plug. U.S. Pat. No. 6,454,811 to Sherwood, et al. discloses devices for tissue engineering that have a gradient of materials, macroarchitecture, microarchitecture, or mechanical properties that can be used to select or promote attachment of specific cell types prior to or following implantation.

While the above describe advances in the art, room for improvements exists. For instance, what is needed in the art are osteochondral implants that can encourage the growth and development of two different tissue types immediately adjacent to one another while being securely held in place in an osteochondral defect. What are also needed in the art are implants that can encourage adequate flow of nutrients to and waste from cells throughout a developing tissue culture, and thus avoid necrosis at the center of the developing tissue culture.

SUMMARY

According to one embodiment, disclosed is an osteochondral construct that can include a cartilage portion, a bone portion, and a polymeric anchor. The cartilage portion can be formed of a hydrogel. The bone portion can include at least one capillary channeled fiber that defines a fluid conduit within the bone portion, which is adjacent to the cartilage portion. The capillary channeled fiber can provide one or more fluid conduits through the bone portion to, e.g., deliver nutrients and/or cells and remove wastes from a developing cellular construct. The polymeric anchor can be adjacent to at least one of the bone portion and the cartilage portion, and can provide a pressure fit between the osteochondral construct and a surrounding structure.

In addition to one or more capillary channeled fibers, the bone portion can also include a polymer/ceramic composite material including a biocompatible polymer and a calcium phosphate ceramic, for instance hydroxyapatite and/or tricalcium phosphate.

An osteochondral construct can have any of a variety of geometries. For instance, the bone portion can be between the cartilage portion and the polymeric anchor. Alternatively, the polymeric anchor can encircle a portion of the cartilage portion or the bone portion.

A construct can be loaded with beneficial materials. For example, a cartilage portion comprising can be loaded with a cell such as a chondrocyte or an undifferentiated mesenchymal stem cell. A bone portion can be loaded with a cell such as an osteocyte or an osteoblast. Any or all of the portions of a construct can be loaded with the same or different bioactive agents.

Also disclosed is a method for forming an osteochondral construct. For example, a method can include incorporating at least one capillary channeled fiber into a bone portion of the construct, adhering a cartilage portion to the bone portion, and adhering a polymeric anchor to at least one of the bone portion and the cartilage portion.

For instance, two portions can be separately formed and then adhered to one another, or one portion can be formed so as to incorporate a terminal portion of an adjacent portion during the formation.

BRIEF DESCRIPTION OF THE FIGURES

The presently disclosed subject matter may be better understood with reference to the Figures, of which.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made to the disclosed subject matter without departing from the scope or spirit of the disclosure. For instance, features illustrated or described as part of one embodiment may be used with another embodiment to yield a still further embodiment.

In general, the present disclosure is directed to osteochondral constructs that can be utilized to encourage both bone and articular cartilage tissue repair in synovial joints. Disclosed constructs are composites including a hydrogel-based portion for implant in a cartilage defect site and an adjacent polymeric/ceramic portion for implant in a bone defect site. Disclosed constructs also include a polymeric anchor that can secure the construct at the desired site. Beneficially, the bone and cartilage portions of disclosed constructs need not be tightly pressure fit into a defect. Pressure fitting as has been utilized with previously known constructs can cause poor integration of new tissue as well as tissue death. Use of disclosed constructs can improve integration of developing tissue with the surrounding implant area.

Disclosed constructs can also include one or more fluid conduits within the bone portion of the construct that can provide improved nutrient flow to and waste flow from tissue developing at the implant site.

Figure 1:
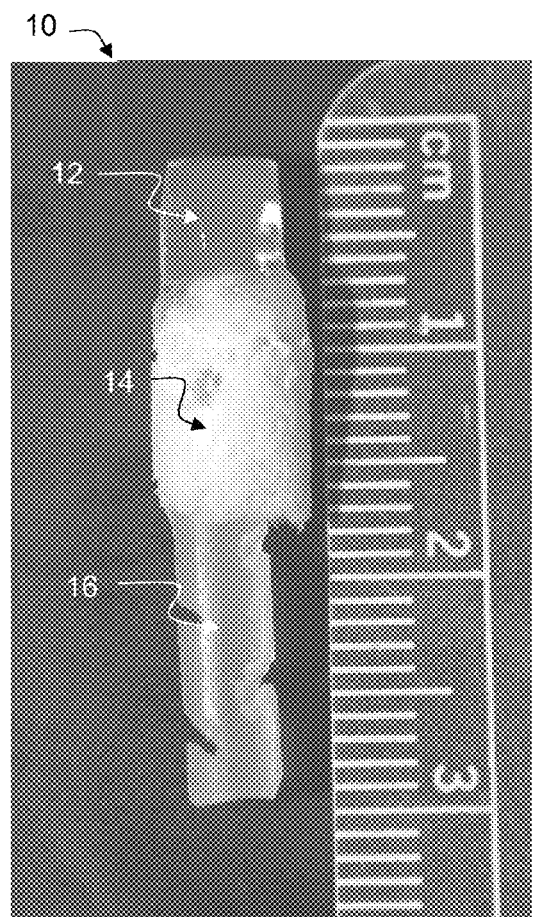
FIG. 1 illustrates one embodiment of an osteochondral construct as disclosed herein.
Figure 2:
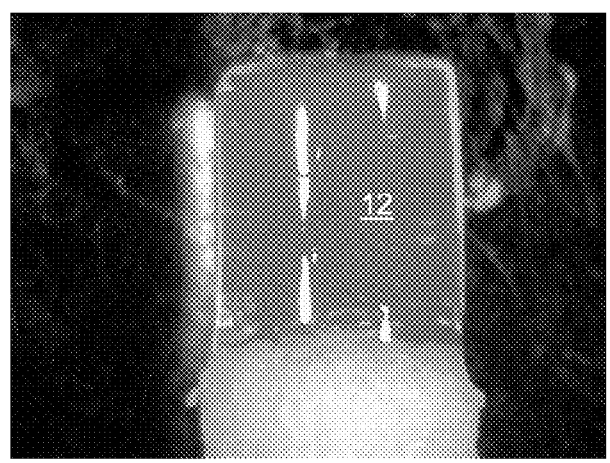
FIG. 2 illustrates the cartilage portion of the construct of FIG. 1.

Referring to FIG. 1, one embodiment of an osteochondral construct 10 is illustrated. Construct 10 includes a cartilage portion 12, which, upon implantation, can be located within an articular cartilage defect in a synovial joint. A larger view of cartilage portion 12 is seen in FIG. 2.

Cartilage portion 12 can be formed from a biocompatible hydrogel and in one embodiment, an implantable hydrogel. For instance, cartilage portion 12 can be formed of a biodegradable hydrogel. Hydrogels are highly absorbent multi-phase systems including a dispersed phase distributed in a continuous phase. For example, the continuous phase can be three-dimensional and/or polymeric in nature, and the dispersed phase can be aqueous in nature. Beneficially, hydrogels are highly absorbent and the polymeric matrix of a hydrogel can be highly hydrated while maintaining structural stability. For instance, the amount of water absorbed by and dispersed within the continuous phase can be many times the weight of the continuous phase.

Suitable hydrogel cartilage portions 12 can include uncrosslinked and crosslinked matrices. In addition, a crosslinked matrix of hydrogel cartilage portion 12 can optionally include hydrolyzable portions, such that the portion can be degradable following implant. For example, in one embodiment, the hydrogel of cartilage portion 12 can include a hydrolyzable cross-linking agent, such as polylactide. The crosslink density can be designed according to standard methods as are generally known in the art to control the rate of degradation of the cartilage portion 12 following implant.

A hydrogel cartilage portion 12 can include natural polymers such as glycosaminoglycans, polysaccharides, proteins, and the like, as well as synthetic polymers, as are generally known in the art. A non-limiting list of hydrophilic polymeric materials that can be utilized in forming hydrogels of a cartilage portion 12 can include dextran, hyaluronic acid, chitin, heparin, collagen, elastin, keratin, albumin, polymers and copolymers of lactide, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins, peptides and polysaccharides such as agarose, and the like.

A hydrogel cartilage portion 12 can be formed according to any method as is generally known in the art. For instance, a hydrogel can self-assemble upon mere contact of the various components or upon contact in conjunction with the presence of particular external conditions (such as temperature or pH). Alternatively, assembly can be induced according to any known method following mixing of the components. For example, step-wise or chain polymerization of multifunctional monomers or macromers can be induced via photopolymerization, temperature dependent polymerization, and/or chemically activated polymerization. Optionally, a hydrogel can be polymerized in the presence of an initiator. For example, in one embodiment, a hydrogel can be photopolymerized in the presence of a suitable initiator such as Irgacure® or Darocur® photoinitiators available from Ciba Specialty Chemicals. In another embodiment, a cationic initiator can be present. For example, a polyvalent elemental cation such as $Ca^{2+}$, $Mg^{2+}$, $Al^{3+}$, $La^{3+}$, or $Mn^{2+}$ can be used. In another embodiment, a polycationic polypeptide such as polylysine or polyarginine can be utilized as an initiator.

The components of a hydrogel cartilage portion 12 can also be designed so as to be self-assembling. For example, following formation of a bone portion 14 (discussed further below), a hydrogel precursor can be applied in a mold at one end of the formed bone portion, and the hydrogel matrix can self-assemble. For instance, the hydrogel precursor can include self-assembling biopolymers such as collagens, laminins, pro-elastin peptides, and the like. Optionally, a self-assembling hydrogel precursor can include polymers that can array themselves according to domains. For example, hydrophilic, relatively charge-neutral synthetic polypeptides such as polyglycine or polylysine can be modified to function in this capacity. Polypeptides can be crosslinked by using carboxy-activating crosslinking agents such as water-soluble carbodiimides. Such cross-linking agents can be used to attach self-assembling proteins or other self-assembling macromolecules to the polypeptides. One example of this approach includes formation of a carbodiimide linkage of collagen or laminin with polylysine. Other hydroxylated entities can be linked in a similar manner. For example, in one embodiment, polyvinyl alcohol can be linked with polypeptides using an epoxy-activation approach or crosslinked via polymerizable methacrylate groups along its side chains, as is known in the art.

In another embodiment, a self-assembling hydrogel can be generated by use of precursors that have been derivatized to contain favorably reactive groups. For example, a hydrogel of this type could be assembled using a first precursor derivatized with a particular reactive moiety and a second precursor derivatized with or comprising a second moiety that can preferentially react with the first moiety on the first precursor. Likewise, other such hydrogels could be generated using such reactive pairs wherein the two moieties that react to form the bond are each conjugated to the same or a different type of polymer. For example, the pairs can be antibody-antigen pairs or avidin-biotin (e.g. streptavidin-biotin).

The hydrogel of the cartilage portion 12 can be porous. For example, a hydrogel cartilage portion 12 can have a porosity of between about 30 and about 90 vol. %, the pores of which can be between about 50 and about 250 μm.

Cartilage portion 12 can include any of a variety of biologically active agents and additives. For instance, cartilage portion 12 can be seeded with cells, e.g., chondrocytes and/or undifferentiated mesenchymal stem cells, to encourage development of a healthy cartilage tissue construct at the implant site. Other materials that can be incorporated in cartilage portion 12 can include growth factors, nutrients, and the like, to encourage growth and development of a tissue construct on the hydrogel scaffolding of cartilage portion 12. For example, cartilage portion 12 can be formed to include hormones; analgesics; anti-inflammatory agents; growth factors; chemotherapeutic agents; anti-rejection agents; RGD peptides, and so forth. In one embodiment, cartilage portion 12 can include as an additive Transforming Growth Factor-beta (TGF-β).

Referring again to FIG. 1, adjacent cartilage portion 12 construct 10 includes a bone portion 14. Following implant, bone portion 14 can be located in a subchondral bone with the portion of construct 10 at which cartilage portion 12 and bone portion 14 meet approximately even with the epiphyses of the joint end of the bone.

In the embodiment of FIG. 1, bone portion 14 can include a polymer/ceramic composite material that can encourage the growth and development of bone tissue thereon. Polymer/ceramic composites as can be utilized in one preferred embodiment of the disclosed constructs can provide the structural stability and controlled degradation rate of implantable polymers in conjunction with improved osteogenesis through inclusion of a calcium phosphate mineral phase in the portion. For instance, polymer/ceramic composites as disclosed by Laurencin, et al. (U.S. Pat. No. 5,626,861), Laurencin, et al. (U.S. Pat. No. 5,866,155), and Armstrong, et al. (U.S. Pat. No. 6,417,247), all of which are incorporated herein by reference, can be utilized in the disclosed constructs.

Biocompatible polymers of the bone portion 14 can include polyanhydrides; polyorthoesters; polyphosphazenes; polyhydroxy acids such as polylactide (PLA), polyglycolic acid (PGA), and polycaprolactone (PCL); aliphatic polyesters; poly(amino acids); polyalkylene oxalates; polyamides; poly(iminocarbonates); polyoxaesters; polyamidoesters; polyarylates; polyhydroxyalkanoates; polysaccharides; copolymers thereof, blends thereof, and the like. In general, any synthetic polymers approved for human clinical use can be utilized. For instance, polymers utilized in medical and pharmaceutical applications such as surgical suture materials and in controlled release devices can be utilized.

In one embodiment, copolymers of polylactide can be utilized. For instance copolymers of polylactide and polycaprolactone (e.g., ε-polycaprolactone), polyglycolic acid, trimethylene carbonate, or p-dioxanone can be utilized in forming a polymer/ceramic bone portion 14. These copolymers are biocompatible and bioresorbable in that their degradation products are low molecular weight compounds such as lactide and glycolic acid that can enter into normal metabolic pathways. Furthermore, copolymers of polylactide can offer the advantage of a large spectrum of degradation rates from a few days to years by simply varying the copolymer ratio of lactide to glycolic acid.

In one embodiment, polymers of a bone portion 14 can include lactide polymers such as poly(L-lactide) (PLLA), poly(DL-lactide) (PLA), and copolymers thereof including poly(lactic-co-caprolactone) (PL/PCL). The co-monomer (lactide:caprolactone) ratios of a PL/PCL copolymer can generally be between about 100:0 and about 50:50. For example, the co-monomer ratios can be between about 85:15 and about 50:50. Blends of PLA with PCL can also be utilized, for instance a PLLA:PCL blend at a ratio between about 85:15 and 50:50 can be utilized.

Bone portion 14 can also include a calcium phosphate ceramic. By way of example, a polymer/ceramic bone portion can include hydroxyapatite (HA) or another calcium phosphate ceramic that includes tricalcium phosphate (TCP) or calcium phosphate ($CaPO_4$).

Calcium phosphate ceramics of a construct 10 can be natural or synthetic materials, as desired. Calcium phosphates occur naturally as geological deposits and in normal biological tissues, principally bone, cartilage, enamel, dentin, and cementum of vertebrates. Synthetic HA can be formed either as pure $Ca_{10}(PO_4)_6(OH)_2$ or can be formed to include ions such as carbonate, fluoride, or chloride, crystals deficient in calcium or crystals in which calcium is partly or completely replaced by other ions such as barium, strontium and lead.

A polymer/ceramic composite can include crystals of calcium phosphate ceramic, e.g., HA, as small, irregularly shaped, thin plates whose rough average dimensions are approximately 10 to 50 angstroms in thickness, about 30 to 150 angstroms in width, and about 200 to 600 angstroms in length. Accordingly, a composite bone portion 14 can include via the ceramic component a large surface area to present to extracellular fluids. This can encourage the rapid exchange of ions with the extracellular fluids and improved healing.

In one embodiment, HA can be incorporated in bone portion 14 in the form of particles having an average diameter between about 10 and about 100 microns, for example about 50 μm in diameter. Mixtures of ceramic particles can also be utilized. For example, TCP particles sized to be selectively dissolved over time and produce voids in the implanted structure can be mixed with HA particle sized to crystallize under physiological conditions to provide a mineral matrix to encourage osteoconduction and osteogenesis at the implant site.

In another embodiment, other ceramics can be incorporated in bone portion 14. For instance a polymer/ceramic bone portion 14 can include magnesium phosphates, aluminas, and the like in an application in which degradation and resorption of the ceramic component of a construct 10 is not desired.

Additional materials can be incorporated into a polymer/ceramic bone portion 14. For instance, other osteoconductive material such as calcium sulfate, bioactive glasses and glass-ceramics, animal derived structural proteins such as collagen, demineralized bone matrix, and so forth, can be incorporated in bone portion 14.

Other bioactive agents can be incorporated into construct 10, for instance in bone portion 14, in cartilage portion 12, or in both, including, by way of example, living cells (e.g., osteoblasts, osteocytes, etc.), proteins and peptides, polysaccharides, nucleic acids, lipids, and non-protein organic and inorganic compounds. Additives can include those that can exhibit biological effects such as osteogenic additives, osteoinductive additives, osteoconductive additives, growth factors, differentiation factors, steroid hormones, cytokines, lymphokines, antibiotics, and angiogenesis promoting or inhibiting factors and so forth.

To promote cell attachment, cell adhesion factors such as laminin, pronectin, or fibronectin or fragments thereof, e.g. arginine-glycine-aspartate, may be coated on or otherwise incorporated on or in a construct. A construct may also be coated or have incorporated therein cytokines or other releasable cell stimulating factors such as; basic fibroblast growth factor (bFGF), transforming growth factor beta (TGF-β), nerve growth factor (NGF), insulin-like growth factor-1 (IGF-1), growth hormone (GH), multiplication stimulating activity (MSA), cartilage derived factor (CDF), bone morphogenic proteins (BMPs) or other osteogenic factors, anti-angiogenesis factors (angiostatin), vascular endothelial growth factor, platelet-derived growth factor and insulin-derived growth factors (IGF).

DNA of a gene sequence, or portion thereof, coding for a growth factor or other of the auxiliary factors mentioned above may also be incorporated into a device or added to a device before or after placement in the body. The DNA sequence may be "naked" or present in a vector or otherwise encapsulated or protected. The DNA sequence may also represent an antisense sequence of a gene or portion thereof.

In addition, either exogenously added cells or exogenously added factors including genes may be added to an implant before or after its placement in the body. Such cells include autograft cells which are derived from a patient's tissue and have (optionally) been expanded in number by culturing ex vivo for a period of time before being reintroduced. Cartilage tissue may be harvested and the cells disaggregated there from and cultured to provide a source of new cartilage cells for seeding a device. A device may also be seeded with cells ex vivo and implanted with live cells attached thereto.

Additives can also include tracking or monitoring agents such as, without limitation, radiopaque materials such as barium, or other imaging agents.

It should be understood that any additive is not limited to any specific portion of the disclosed inserts. Additives as disclosed above may be incorporated in any suitable portion of a disclosed insert, as is known to one of ordinary skill in the art.

Figure 3:
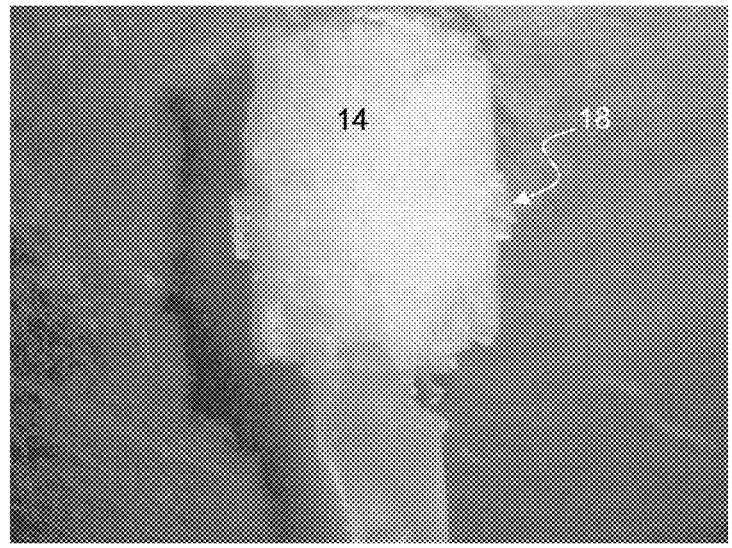
FIG. 3 illustrates the bone portion of the construct of FIG. 1.

Referring to FIG. 3, bone portion 14 of construct 10 can also include one or more fluid conduits 18 incorporated in the composite structure. Fluid conduits 18 can improve materials transfer from surrounding tissue to a developing tissue construct within bone portion 10. More specifically, fluid conduits 18 can provide for adequate oxygen and nutrient transfer to cells developing on construct 10 and adequate waste dispersion from such cells. Accordingly, as tissue develops on construct 10, the inclusion of fluid conduits 18 in construct 10 can prevent necrosis of new cells within the center of the tissue construct. In one embodiment as illustrated in FIG. 3, bone portion 14 can include a small bundle of between 1 and about 5 capillary channeled fibers that provide fluid conduits 18 extending across a width of bone portion 14.

Figure 4:
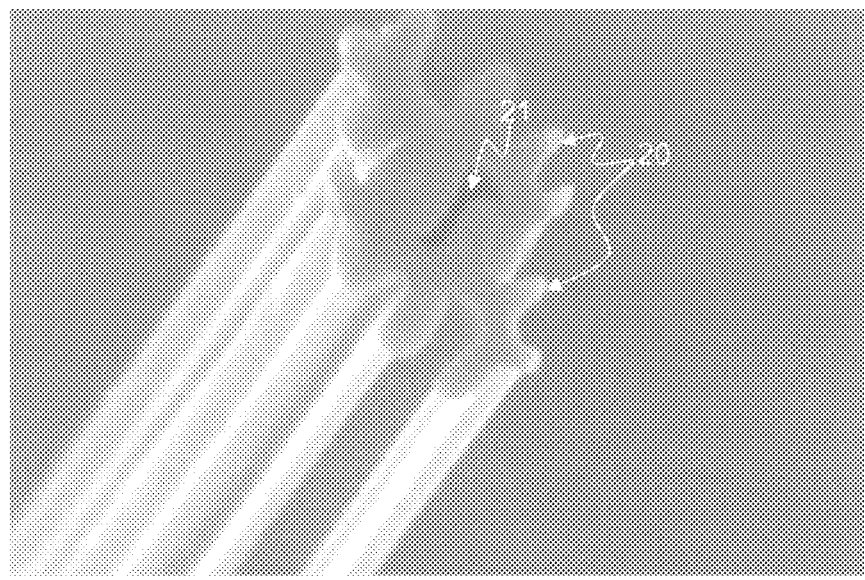
FIG. 4 illustrates capillary channeled fibers as may be incorporated in a construct as disclosed herein.

FIG. 4 illustrates two capillary channeled fibers 20 as may be utilized as fluid conduits 18. By way of example, suitable capillary-channeled polymer fibers include, but are not limited to, fibers as described in U.S. Pat. Nos. 5,200,248 to Thompson, et al., and 5,972,505 to Phillips, et al., the entirety of each of which is incorporated herein by reference. Other types of non-circular cross section fibers suitable for use in connection with the present invention include, but are not limited to COOLMAX® and ANTRON® fibers, which are manufactured by Invista of Waynesboro, Va.; HIGH-LIGHTS™ fibers, which are manufactured by Superior Threads of St. George, Utah; and 4DG™ fibers, available from Fiber Innovation Technology of Johnson City, Tenn.

Polymers as may be utilized to form a capillary channeled fiber 20 can include degradable or non-degradable biocompatible polymers, depending upon the desired application of the construct 10. Examples of suitable polymers include, but are not limited to, polyesters, polylactides, poly-β-hydroxybutyrates, polycaprolactones, polyglycolides, polyetheresters, rayon, acetate, polyamides (e.g., nylon), polyolefins, polyacrylates, polydioxanones, polytrimethylene carbonates, polyanhydrides, polycarbonates, polylactides, polyoxyalkylene ether, alkylene oxide compounds, polysaccharides, polyphosphazenes, polyethylene oxide-polypropylene glycol block copolymers, fibrin, polyvinyl pyrrolidines, hyaluronic acid, collagen, chitosan, polyvinyl alcohol, copolymers and blends of such polymers, and the like. In one embodiment, fiber 20 can be formed of the same polymer as the polymer component of the polymer/ceramic composite of bone portion 14.

Capillary channeled fiber 20 defines a non-circular cross section including a plurality of co-linear channels extending the entire length of the exterior surface of the fiber 20. Each channel is defined by a pair of opposed walls that extend generally and longitudinally and form part of the exterior surface of the fiber 20. Desirably, these channels and walls extend down the entire length of the fiber 20 parallel to the longitudinal axis of the fiber 20 and are co-linear on each fiber 20. This produces de facto substantially the same co-linear channels across the width of bone portion 14 in the specific embodiment of FIG. 1 and FIG. 3.

There are different fabrication approaches to form channeled polymer fibers 20 of the sort demonstrated herein. For instance, extrusion processes as are generally known in the art can be employed in the manufacture of a capillary channel fiber 20. For example, extrusion processes, such as melt spinning, wet spinning, and dry spinning, can be used. Melt-spinning can be used in one preferred embodiment. In general, melt spinning involves melting the polymer, applying pressure to extrude the melt through the extrusion die, and cooling and drawing the extruded structure to the desired size. Melt spinning and other spinning methods each involve the use of an extrusion die (sometimes referred to as a spinneret) which has an orifice design which roughly corresponds to the cross-sectional shape of the capillary channeled fiber immediately upon exit from the die. Depending upon orifice design, processing conditions, polymer composition, and other factors known to those skilled in the art, the final cross-sectional shape of a fiber can deviate from the orifice design. The extrusion die orifice design, the polymer, the temperature at which it is molten for extrusion, and processing conditions of the extruded polymer during drawing and cooling can be of importance in forming a capillary channeled fiber 20.

In order for the extruded, but not yet cooled, structure to better retain its shape and capillary wall and base element dimensions relative to the capillary channel size approximate to that of the extrusion die orifice, the polymer can be extruded at low temperature relative to the temperatures conventionally preferred for extrusion of the particular type of polymer in conventional fiber extrusion processes. The extruded polymer can then be cooled relatively rapidly during a drawing process for shape retention.

A polymer forming a capillary channeled fiber can be of an amorphous or semicrystalline character. Amorphous and semicrystalline polymers can resist breakage upon drawing over a relatively large temperature range, particularly as temperature approaches the glass transition temperature. Whereas such polymers are commonly extruded at relatively high temperatures, to reduce viscosity of the melt and consequently facilitate higher extrusion die polymer throughput, improved shape retention of the capillary channel structures (relative to the extrusion die orifice design) can be obtained by operating at temperatures closer to the glass transition point. The optimal temperatures for extrusion will vary from polymer to polymer.

The channels of a fiber 20 can be designed so as to encourage flow therethrough via capillary action to provide fluid flow through a bone portion 14. For instance, a capillary channeled fiber 20 can have channel wall thicknesses of less than about 50 µm, less than about 10 µm, or less than about 5 µm, in one embodiment. The width of an individual channel can generally be less than about 0.5 mm, for instance less than about 0.3 mm, or less than about 0.1 mm. Channel widths from about 5 µm to about 0.5 mm will typically be used, more typically from about 30 µm to about 100 µm. The individual channels of a fiber 20 can generally be between about 15 µm and about 50 µm in depth, i.e., the height of the walls defining a channel there between. The capillary channels can be of any suitable shape. For instance a channel can define a regular cross-sectional shape (e.g., U-shaped, V-shaped, etc.), or can be irregular in cross-sectional shape. Generally, the capillary channels of a fiber can be of regular cross-sectional shape, with capillary channel walls that are substantially parallel to one another in cross-section. The capillary channel walls can be substantially perpendicular to the straight chords closing the capillary channels to which the wall serves as a boundary, though this is not required in the disclosed constructs.

In one preferred embodiment, a capillary channeled fiber 20 can satisfy the equation:

$$(1 - X\cos(\theta_a)) < 0,$$

wherein $\theta_a$ is the advancing contact angle of water measured on a flat film of the same material make-up as the fiber, X is a shape factor of the fiber cross-section that ranges from about 1.2 to about 5 and satisfies the equation $$X = \frac{P_W}{4r + (\pi - 2)D}$$

wherein $P_w$ is the wetted perimeter of the fiber, r is the radius of the circumscribed circle circumscribing the entire fiber cross-section, and D is the minor axis dimension across the fiber cross-section.

In another embodiment, a fiber can satisfy the equation $$(1 - X\cos(\theta_a)) < -0.7.$$

Capillary channeled fibers can encourage flow through the channels of the fiber for delivery of materials, e.g., nutrients, cells, etc. to a developing cellular construct on a bone portion 14 as well as for removal of waste products from cells on a bone portion 14. In one preferred embodiment, a bundle of two or more capillary channeled fibers 20 can be utilized, as is illustrated in FIG. 4. As can be seen, when bundled together, the bundle includes the channels of each fiber as well as a closed channel 21 formed between the two adjacent fibers. Closed channel 21 can function as a conduit to carry materials through a bone portion in a semi-isolated state. Specifically, channel 21 can function as a closed channel, but can still maintains communication and interaction with the surroundings due to the junctions formed between the adjacent fibers. Thus, a channel 21 formed between adjacent fibers can provide both the fluid transport properties of a closed channel and interaction with the surrounding environment of an open channel.

Fluid conduits as provided by, e.g., capillary channeled fibers 20, can also include biologically active agents as described above as additives. For instance, degradable capillary channeled fibers can include growth factors, antibiotic agents, and the like incorporated within the fiber structure that can leach out of the fiber for release or can be released as a fiber degrades.

Biologically active agents can also or alternatively be located on the surface of a fiber according to any suitable coating or surface application process. For instance, biologically active agents can be temporarily or permanently bonded to a capillary channeled fiber 20. In general, an agent can be bonded to a fiber via an existing chemical functionality of the agent, such as amine, carboxylate, or thio groups, that can allow covalent, non-covalent, charge/charge, or any other type of bonding of the agent to a fiber surface while maintaining the chemical activity of the agent. In such an embodiment, the base fiber composition can be selected so as to incorporate an anchoring mechanism for the agent. By way of example, a biologically active agent that includes a protonated amine functionality can be bonded to a polymeric fiber surface including negative charge groups.

Surface chemistry modification of a fiber can also be carried out to encourage bonding of a biologically active agent to the fiber. Fiber surface chemistry modification processes can include, without limitation, alkaline treatments, plasma treatments, and the like. Fiber surface modification can encourage bonding of an active agent to the surface via any means. For example, fiber surface modification can increase the number of carboxylate groups on a fiber surface available for bonding to a desired active agent.

According to one embodiment, a grafting process may be employed for functionalizing a fiber surface with a desired chemistry. For instance, an at least bi-functional polymer possessing desired reactive functional groups such as carboxy, anhydride, amino or hydroxy groups may be first grafted to a fiber surface utilizing a portion of the functional groups of the polymer. Remaining functional groups of the polymer may then be utilized to attach additional functional materials to the fiber surface, e.g., biomolecules, micro-particles, nano-particles, and the like. For example, a poly(ethylene terephthalate) (PET) fiber can be modified to include a polyacrylic acid layer, with further functionalization as desired to incorporate specific biologically active agents at the fiber surface. Surface modification of substrates in accordance with this grafting process is taught by U.S. Pat. No. 7,026,014 to Luzinov, et al., the entirety of which is incorporated herein by reference.

Direct surface modifications can also be used to establish a surface to which active ingredients can be anchored. For example, a polyamide fiber surface can be treated with ethylene-diamine to form a surface that is rich with both carboxylate and amine functionalities that can then be utilized to bond specific biologically active agents.

Fluid conduits 18 such as may be provided by a bundle of capillary channeled fibers 20 can be located in a bone portion according to any suitable design. In particular, though illustrated in FIG. 1 and FIG. 3 as a single bundle of fibers 20 extending across a width of bone portion 14, the disclosed subject matter is not limited to any particular geometric design for fluid conduits 18. For instance, a fluid conduit can extend partly or completely across a bone portion 14 in any desired direction. Fluid conduits can be located with specific location through out a bone portion 14 and can encourage development of aligned cells along the paths of the conduits. Moreover, a fluid conduit 18 can be formed of a single flow device, e.g., a single capillary channeled fiber, or as a bundles of fibers, as is illustrated in FIG. 1 and FIG. 3.

The porous polymer/ceramic composite of bone portion 14 can be formed according to any method that can produce a porous structure having desired mechanical properties. In general, a porous polymer/ceramic composite of bone portion 14 can define a porosity of between about 10 and about 50 volume %, for instance between about 20 and about 30 volume %, and a pore size of between about 30 µm and about 300 µm, for instance between about 100 µm and about 200 µm.

In one embodiment, a polymer/ceramic composite can be formed according to a sintering technique as described by Robinson, et al. (*Otolaryngol. Head and Neck Surg.* 1995 112: 707-713), which is incorporated herein by reference. According to this method, bulk polymer and ceramic particles are granulated, microsieved, and sintered slightly above the glass transition temperature of the polymer. Sintering causes the adjacent polymer particles to bind at the contact point to produce irregularly shaped pores. Of course, in such an embodiment a fluid conduit would need to be either formed of a material that would not lose its effective shape during a sintering process or alternatively be introduced into the bone portion following the high temperature sintering process.

According to another embodiment, a polymer/ceramic portion can be formed according to a particulate leaching method such as have been described by Mikos et al. (Polymer 1994 35:1068-1077) and Thomson at al. (J. Biomater. Sci. Polymer Edn 1995 7:23-38), both of which are incorporated herein by reference. According to such methods, a matrix can be formed by dissolving a polymer in a solvent followed by the addition of sacrificial particles or microspheres that will later be removed to provide the desired porosity. The composite is molded around the fluid conduits and the solvent allowed to evaporate. The resulting mold can then be heated slightly beyond the $T_g$ for the polymer to ensure complete bonding of the polymer. Once cooled, the particles are leached out to provide a porous matrix.

Laurencin et al. describe a salt leaching/microsphere technique to induce pores into a polymer/ceramic matrix (Devin et al. J. Biomater. Sci. Polymer Edn 1996 7:661-669, incorporated herein by reference) that can be utilized in one embodiment. In this method, an interconnected porous network can be made by the imperfect packing of polymer microspheres. The porous matrix is composed of polymeric microspheres with both sacrificial and ceramic particulates mixed with the polymeric microspheres. Removal of sacrificial particles is used to widen the channels between the polymer microspheres. Ceramic particles are used to provide added support to the matrix and to allow for osteointegration.

In this method, a polymer can be dissolved in a solvent to create a highly viscous solution. A 1% solution of, e.g., poly (vinyl alcohol), is then added to form a water/oil emulsion. Particulates are added to the emulsion and the resulting composite mixture is molded around the fluid conduits, dried, and subjected to a leaching step.

In general, polymers can be dissolved in an organic solvent such as methylene chloride or chloroform to mix with a ceramic and sacrificial particles. In a particulate leaching method, the polymer is dissolved in a solvent that does not adversely affect the polymer or the sacrificial material, e.g., salt or sugar particles, most preferably a volatile organic solvent. The relative amount of solvent will have a minimal effect on the structure of the produced materials, but will affect the solvent evaporation time.

Referring again to FIG. 1, an osteochondral construct 10 can also include an anchor 16. Anchor 16 can be formed of a polymeric, biocompatible material that can exhibit suitable compression so as to provide a pressure fit with surrounding tissue to hold construct 10 at the desired location. Additionally, anchor 16 can be formed of a polymeric material with a relatively low glass transition temperature ($T_g$), for instance less than about 15. Accordingly, at physiological conditions anchor 16 can be somewhat 'sticky' at the surface and can adhere to surrounding tissue.

In one embodiment, anchor 16 can be formed of a polymeric material similar to that of the bone portion 14 of a construct 10. For example, anchor 16 can be formed of biodegradable lactide polymers such as poly(L-lactide) (PLLA), poly(DL-lactide) (PLA), and copolymers thereof including poly(lactic-co-caprolactone) (PL/PCL). The co-monomer (lactide:caprolactone) ratios of a PL/PCL copolymer can generally be between about 100:0 and about 50:50. For example, the co-monomer ratios can be between about 85:15 and about 50:50. Blends of PLA with PCL can also be utilized, for instance a PLLA:PCL blend at a ratio between about 85:15 and 50:50 can be utilized.

Anchor 16 can hold construct 10 securely in place according to two different schemes working in concert with one another. First, anchor 16 can be of a size slightly larger than the hole into which it will be located, so as to provide a high pressure fit of the anchor 16. To that end, anchor 16 can optionally be configured to include one or more barbs, ridges, cuts, and so forth, that can improve the pressure hold between anchor 16 and surrounding tissue. Second, anchor 16 can adhere to surrounding tissue due to the low $T_g$ material used to form anchor 16. For instance, anchor 16 can be formed from a material exhibiting a glass transition temperature $T_g$ of between about −60° C. and about 37° C., or between about −60° C. and about 0° C. Accordingly, through a combination of material design and geometric construction, anchor 16 can firmly contain an osteochondral construct at the desired locale. Due to the exceptional holding capacity of anchor 16, the other portions of the construct, the cartilage portion 12 and the bone portion 14, need not be tightly fit at the implant site. This can further improve the healing and tissue generation capability of disclosed implants. Specifically, in the past, pressure fits were often utilized across an entire implant surface to adequately hold an implant in place. However, high pressure at the interface between an implant and surrounding tissue can inhibit growth and development of healthy tissue at the site. Thus, many previously known osteochondral plug-type inserts exhibited less than desirable integration for in vivo applications, at least in part due to the high pressure at the interface necessary to hold the insert in place.

In forming a unitary osteochondral construct, individual portions can be formed on an adjacent portion or adhered to an adjacent portion following formation, as desired. For instance, in one embodiment a polymeric anchor can be initially formed. A bone portion can then be formed in a mold into which the terminal portion of the anchor is placed. In one embodiment, solvents utilized in forming the polymer/ceramic composite bone portion can cause the terminal portion of the anchor to solubilize and become firmly adhered to the polymer/ceramic composite material of the bone portion. Alternatively, if the terminal portion of the anchor is not solubilized by components used in forming the bone portion, the terminal portion of the anchor can become embedded in the polymer/ceramic composite of the bone portion and thereby tightly adhered thereto via physical embedding.

Following, a cartilage portion can be molded at the appropriate surface of the bone portion. According to this embodiment, the hydrogel material used to form the cartilage portion can mix with material of the bone portion during formation of the hydrogel matrix, and the two portions can include an area of intermix of material between the two. This intermix area can include intermingled both the hydrogel matrix phase of the cartilage portion and the polymer and ceramic phases of the bone portion, which can serve to tightly adhere the two portions to one another.

Alternatively, portions of an osteochondral construct can be adhered to one another utilizing any of a variety of biocompatible, implantable adhesives, as are generally known in the art.

Figure 5:
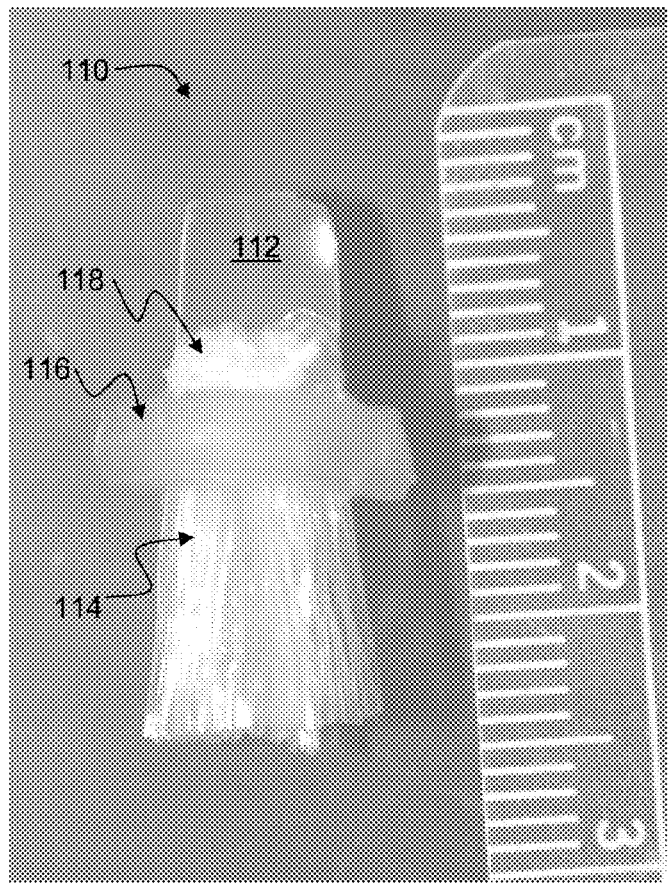
FIG. 5 illustrates another embodiment of an osteochondral construct as disclosed herein.

Referring to FIG. 5 another embodiment of an osteochondral construct 110 is illustrated. According to this embodiment, cartilage portion 112, can be similar to that described above, e.g., an implantable hydrogel including a biodegradable matrix that can be loaded with mesenchymal stem cells, chondrocytes, and/or suitable growth factors and other bioactive agents.

The bone portion 114 of the osteochondral construct 110 includes a plurality of capillary channeled fibers 120. The capillary channeled fibers 120 of bone portion 114 are similar to those described above for use as a fluid conduit in the bone portion 14 of the osteochondral construct 10 of FIG. 1. The bone portion 114, however, does not include the capillary channeled fibers 120 embedded within a porous polymer/ceramic composite. Instead, bone portion 114 includes a large number of capillary channeled fibers 120 that form the bulk of bone portion 114.

Figure 6:
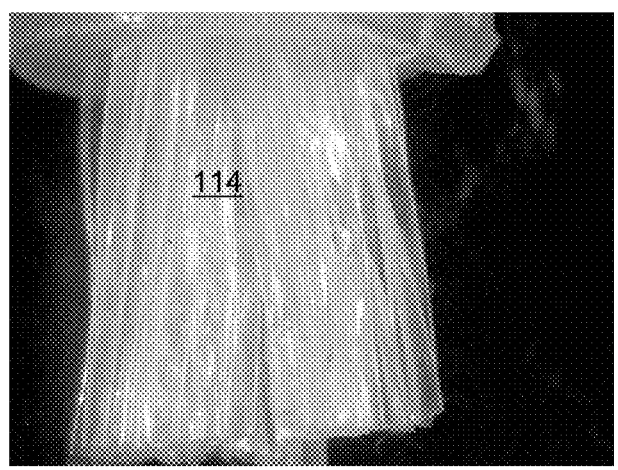
FIG. 6 illustrates the bone portion of the construct of FIG. 5.

Bone portion 114 can include a plurality of capillary channeled fibers 120 in the form of a single, large bundle, or as a plurality of smaller bundles of fibers 120. In the embodiment of FIG. 6, bone portion 114 includes several bundles each including 4 capillary channeled fibers held together in the form of a single bundle, formation of which is described in further detail in the examples section, below. Beneficially, this methodology can provide a route to formation of large constructs capable of encouraging growth and development of new tissue over larger areas of synovial joint damage than has been possible in the past.

Figure 7:
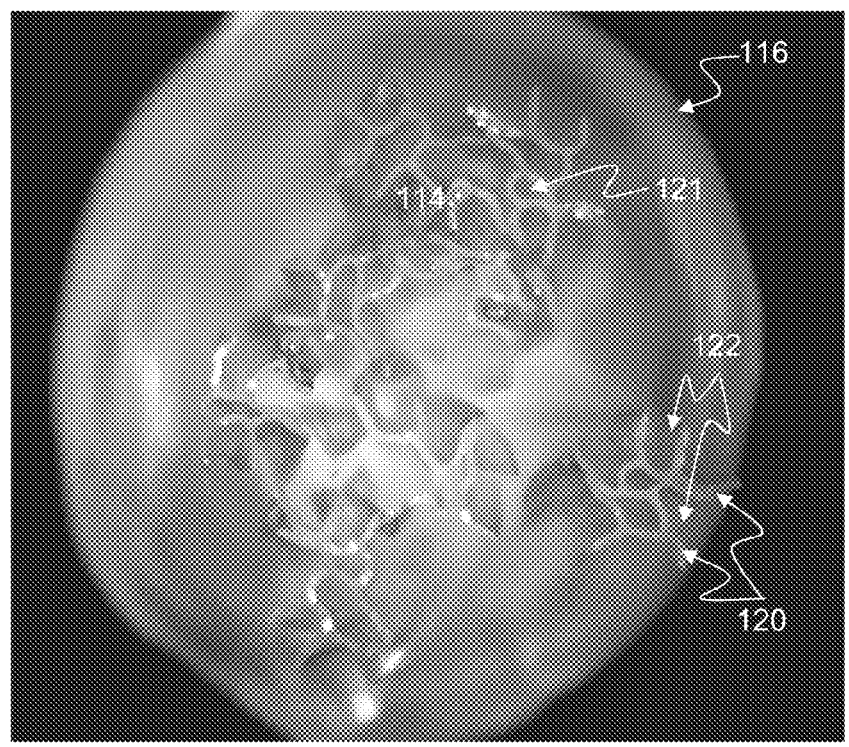
FIG. 7 is an end view of the bone portion of the construct of FIG. 5.

FIG. 7 illustrates bone portion 114 in an end view. As can be seen, individual fibers are loosely held against one another such that the bone portion 114 defines open capillary channels between and among individual fibers. Specifically, bone portion 114 includes both open channels 122 at the outer edge of a bundle and closed channels 121 that are formed between adjacent channels and within a bundle of fibers 120.

The overall shape and dimensions of capillary channeled fibers 120 can be similar to those of fibers 20 described previously, but that is not a requirement of the present disclosure. For instance, capillary channeled fibers 120 can be designed to function as fluid conduits with the dimensions of the individual channels configured to encourage fluid flow therethrough via wicking action, as described above.

In one embodiment the channels of capillary channeled fibers 120 can be configured so as to contain desired additives of bone portion 114. For instance, additives can be included on the surface or in the structure of fibers 120 of bone portion 114 as described above. By way of example, growth factors, nutrients, antibiotics, and the like can be incorporated within the structure of fibers 120 and/or coated on the surface of fibers 120 as previously described. Alternatively or additionally, the channels of capillary channeled fibers 120 can be utilized for loading desired additives on to bone portion 114. For example, mesenchymal stem cells or osteocytes can be loaded into bone portion 114 and specifically, adhered in the channels of capillary channeled fibers 120. Other additives, such as particulate additives, can be similarly loaded into bone portion 114 via the channels of capillary channeled fibers 120. For example, ceramic particles can be held within the channels of capillary channeled fibers 120.

Particulates (e.g., cells or ceramic particles) may be loaded into and/or affixed to the fiber/channel surface by either physical or chemical means. A fiber characteristic of relevance is the relationship between the particle size and the achievable volume/mass loading capacity of the fiber channels. For example, a high particle loading level can be attained when the channel diameter is much larger than the average diameter of the functional particles.

Particle loading mechanisms can include any suitable method including electrospray, dip-coating, flowing slurries, wicking action and the like that are common deposition or loading mechanisms. In the case of dip-coating, the wetting/wicking characteristics of the fiber can be chosen or created to facilitate the process.

Following loading, particles can be bound to an existing or created functional moiety at the surface of a fiber, can be held within the channels of a fiber through surface particle/particle and particle/fiber effects, or can be encouraged to remain within the channels of a fiber through further processing. For example, a loaded fiber can be subjected to a thermal treatment that can soften the polymeric fiber and cause the partial collapse of the channel walls around particles loaded therein. In general, however, further processing is not necessary, and particles loaded into fiber channels will remain therein due to surface effects, e.g., charge/charge interactions and the like.

Referring again to FIG. 5, osteochondral construct 110 includes an anchor 116. Anchor 116 can be formed of materials as described above so as to provide anchoring of construct 110 at an implant site via both pressure fitting and material adherence as described above. Anchor 116 defines an annular shape and can be located near the interface of cartilage portion 112 and bone portion 116. In general, however, anchor 116 can be located somewhat below this interface, such that the pressure fit of anchor 116 will be within the subchondral bone hole of the implant site.

Osteochondral construct 110 can include a portion 118 interposed between bone portion 114 and cartilage portion 112. Portion 118 can be a porous polymer that can be utilized to facilitate the adherence of the multiple fibers of bone portion 114 to the hydrogel of cartilage portion 112. For instance, portion 118 can be formed of the same polymer as bone portion, but formed as a porous plug according to a solvent casting/particle leaching method as described above. Portion 118 can then be adhered to the ends of the fibers forming bone portion and/or the anchor 116. Adherence can be through physical or chemical means. For example, the various portions can be heated to a softening temperature and pressed together to physically adhere the portions to one another.

Optionally, a biocompatible adhesive can be utilized alternatively to or in conjunction with a physical adhesion process.

Cartilage portion 112 can be formed on the surface of portion 118 as described above for osteochondral construct 10 of FIG. 1. Additionally, the hydrogel material used to form the cartilage portion 112 can intermix with the polymeric matrix of portion 118 during formation of the hydrogel matrix, and the two portions can include an area of intermix of material between the two. This intermix area can include intermingled both the hydrogel matrix phase of the cartilage portion and the polymer of portion 118, which can serve to tightly adhere the two portions to one another.

The present disclosure may be better understood with reference to the Examples, below.

EXAMPLE 1

An osteochondral construct similar to that of FIG. 1 was formed.

Initially the anchor portion of the construct was formed. A mold in the shape of the anchor was placed on a compression molding platform that was heated to approximately 140° C. A copolymer of poly-L-lactide and polycaprolactone, 75%/25% respectively (PL/PCL) was placed on the two halves of the mold to allow the polymer to melt and fill in the shape of the mold. The two halves were placed together and compressed by the heated platforms and held for 1 minute. The mold was quenched in water and allowed to cool for 15 minutes following which the mold was taken apart and the anchor was removed.

After forming the anchor, the bone portion of the construct containing the wicking fibers was formed and attach to the anchor. A copolymer of poly-L-lactide and polycaprolactone, 75%/25% respectively (PL/PCL), was added to biotech grade chloroform at a concentration of 0.15 g/mL. The mixture was left overnight to allow the polymer to completely dissolve. Hydroxyapatite powder (HAP) was then added to the solution at a concentration of 10% W/V and mixed with a magnetic stir bar. The previously produced anchor was inserted 2 mm in to the bottom of a Teflon® mold with a diameter of approximately 7 mm. A small bundle of wicking fibers was inserted through the diameter of the mold at the half way mark of the height through holes that were drilled through the wall of the mold.

A volume of 0.5 ml (0.482 g) of glucose, which had been passed through a sieve to extract grain sizes of 250 µm-425 µm, was added to the Teflon® mold, on top of the pin and fibers. A volume of 0.5 ml of the PL/PCL/HAP solution was slowly added on top of the glucose, the mold was covered with parafilm, and two small holes were made in the parafilm to avoid rapid evaporation of the chloroform. The chloroform caused the edges of the pin to solubilize and as the chloroform evaporated the pin became attached to the porous scaffold. The mold was left in a chemical hood for 12 hours to allow the chloroform to evaporate. The scaffolds were then removed from the molds and placed in mesh containers that were suspended in distilled water that was continually stirred with a magnetic stir bar. The scaffolds remained in water for 48 hours, and the water was replenished every 12 hrs. The scaffolds were then removed from the water and allowed to dry for 24 hours. The final product was a porous cylinder scaffold with a fiber bundle running the diameter and a barbed anchor attached to the bottom.

The final step of the formation process was to form the hydrogel that is used for the cartilage portion of the construct. 2% agarose was sterilized in an autoclave, which also allowed for the agarose to dissolve. Following, the agarose was brought back down to 32° C. A cell suspension of mesenchymal stem cells was added to the agarose and mixed to create a uniform distribution of cells. The cell/agarose mixture was placed in a cylindrical mold with a diameter of 7 mm. The bone portion of the construct that was previously formed was inserted in the mold and extended into the agarose approximately 2 mm. The agarose penetrated into the porous scaffold and allowed the two portions to attach to one another. The construct was placed at 2° C. for 10 minutes to allow the agarose to gel.

Following formation, the bone portion of the construct can be seeded with mesenchymal stem cells.

Pull out tests were performed on the formed constructs to determine the stability of the anchoring system. The results were then compared to the pull-out strength of press fit osteochondral grafts as described by Duchow, et al. (*American Journal of Sports Medicine*, 2000, 28(1), p. 24-27) to determine if the barbed pin would secure the construct as well as press fitting would.

Porcine hind legs were obtained and each knee was separated to expose the femoral condyles, the distal portion of the femur was removed from the rest of the bone, and excess soft tissue was removed. Recipient sites of 10-mm depth and diameter of 7 mm were drilled on the articulating surface of the femoral condyles. The site was then irrigated to prepare for the insertion of the constructs. The condyles were then placed in an Instron Model 5944 tester. To avoid external compression to the construct, the bottom of the drill hole was placed well above the clamp fixing the specimen in the testing machine. The graft was then inserted into the site. To prepare for the pull-out test, a small wire was cast into the barbed pin and the top of the wire was clamped in the upper crosshead of the Instron. A tensile load was applied at a rate of 10 mm/minute and the pull-out strength was determined. Five samples were tested.

Figure 8:
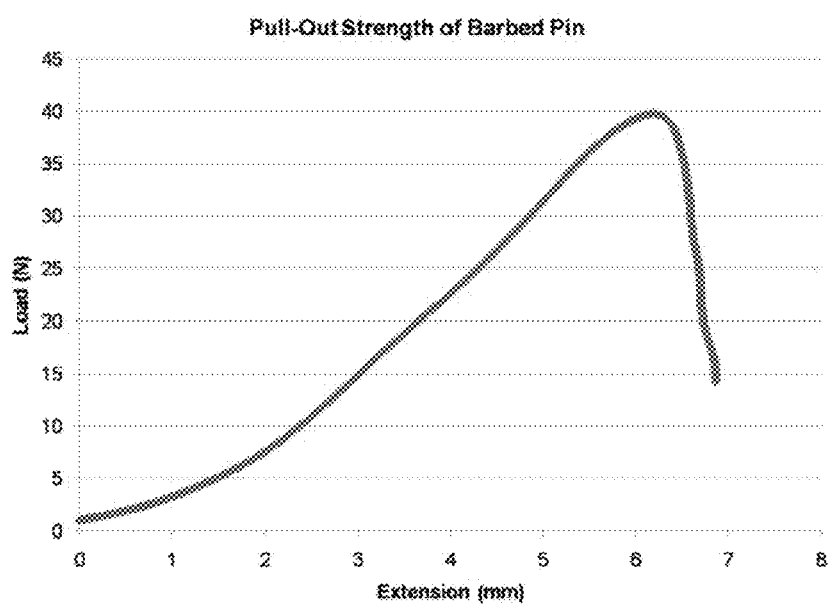
FIG. 8 graphically illustrates the pull-out strength of a construct as described herein.

An example of the typical load-extension curve from the pull-out tests is shown in FIG. 8. The average pull-out strength of the barbed pin was $37.3 \pm 7.2$ N (Table 3.3). This value is not statistically different ($p<0.05$) than the average pull out strength of comparison osteochondral grafts with diameters of 8 mm, i.e. $41 \pm 21$ N as reported by Duchow and coworkers previously cited.

EXAMPLE 2

The objective of this study was to use an osteochondral construct to generate and characterize engineered osteochondral tissue. The study consisted of stem cells cultured on a barbed pin design osteochondral construct as described above in Example 1. The biphasic constructs were cultured in a static system and also in a modified bioreactor that is able to apply fluid flow and hydrostatic pressure to each phase of the construct. Human mesenchymal stem cells (hMSCs) were used to determine if the findings from the murine studies would translate to human cells.

Figure 9:
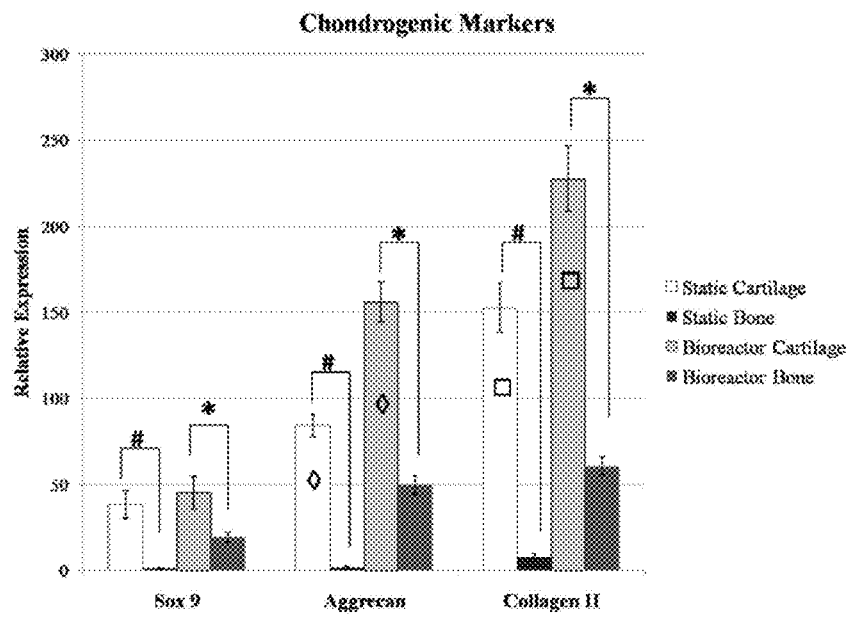
FIG. 9 illustrates results of real time RT-PCR for the chondrogenic markers sox9, aggrecan and collagen Type II in a stem cell study of a construct as disclosed herein.

The results of the real time RT-PCR for the expression of chondrogenic markers are shown in FIG. 9. The results were reported as relative expression to GAPDH using the $\Delta\Delta Ct$ method. Error bars represent the standard deviation. Pound symbols (#) signify significant differences ($p<0.05$) between relative expressions of chondrogenic markers in the static cartilage samples and the static bone samples. Asterisks (*) signify statistically significant differences ($p<0.05$) between relative expressions of chondrogenic markers in the cartilage phases and bone phases cultured in the bioreactors. Squares and diamonds (□, ◊) signify statistically significant differences ($p<0.05$) between relative expressions of chondrogenic markers in the static cartilage samples and the cartilage phase of the constructs cultured in the bioreactors.

All of the cartilage samples showed high levels of expression of the chondrogenic markers. The static cartilage samples showed significantly higher expression of all three markers, sox9, aggrecan, and collagen type II, than the static bone samples. The cartilage phase of the constructs cultured in the bioreactor showed a higher expression of all three markers, sox9, aggrecan, and collagen type II, than the bone phase of the constructs cultured in the bioreactor. In addition, the cartilage phases cultured in the bioreactor showed higher aggrecan and collagen type II expression as compared to the static cartilage samples.

Figure 10:
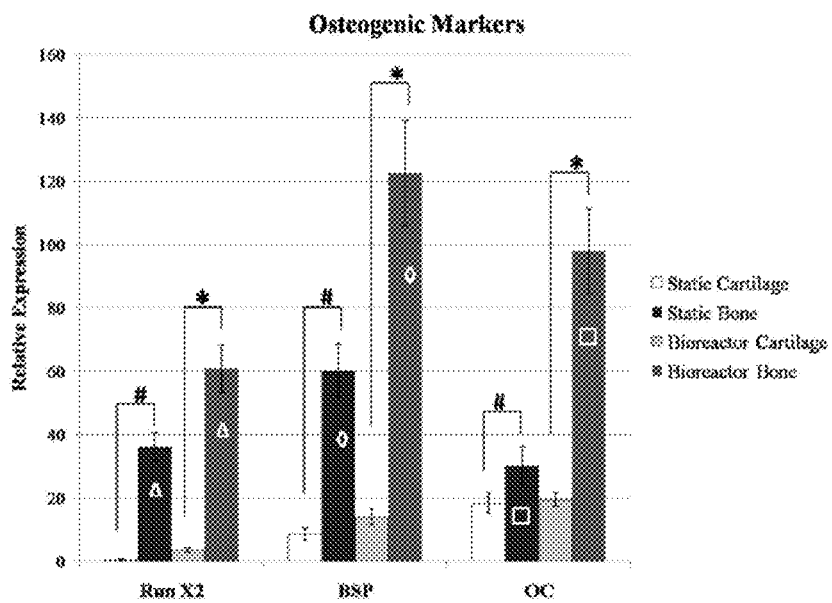
FIG. 10 illustrates results of real time RT-PCR for the osteogenic markers RunX2, bone sialoprotein and osteocalcin in the stem cell study.

The results of the real time RT-PCR for the expression of osteogenic markers are shown in FIG. 10. The results are reported as relative expression to GAPDH using the ΔΔCt method. Error bars represent the standard deviation. Pound symbols (#) signify significant differences (p<0.05) between relative expressions of osteogenic markers in the static bone samples and the static cartilage samples. Asterisks (*) signify statistically significant differences (p<0.05) between relative expressions of osteogenic markers in the bone phases and cartilage phases cultured in the bioreactors. Squares, diamonds, and triangles (□, ◇, Δ) signify statistically significant differences (p<0.05) between relative expressions of osteogenic markers in the static bone samples and the bone phase of the constructs cultured in the bioreactors.

All of the bone samples showed high levels of expression of the osteogenic markers. The static bone samples showed significantly higher expression of all three markers, RunX2, BSP, and OC, than the static cartilage samples. The bone phase of the constructs cultured in the bioreactor showed a higher expression of all three markers than the cartilage phase of the constructs cultured in the bioreactor. In addition, the bone phases cultured in the bioreactor showed higher RunX2, BSP, and OC expression as compared to the static bone samples.

Figure 11:
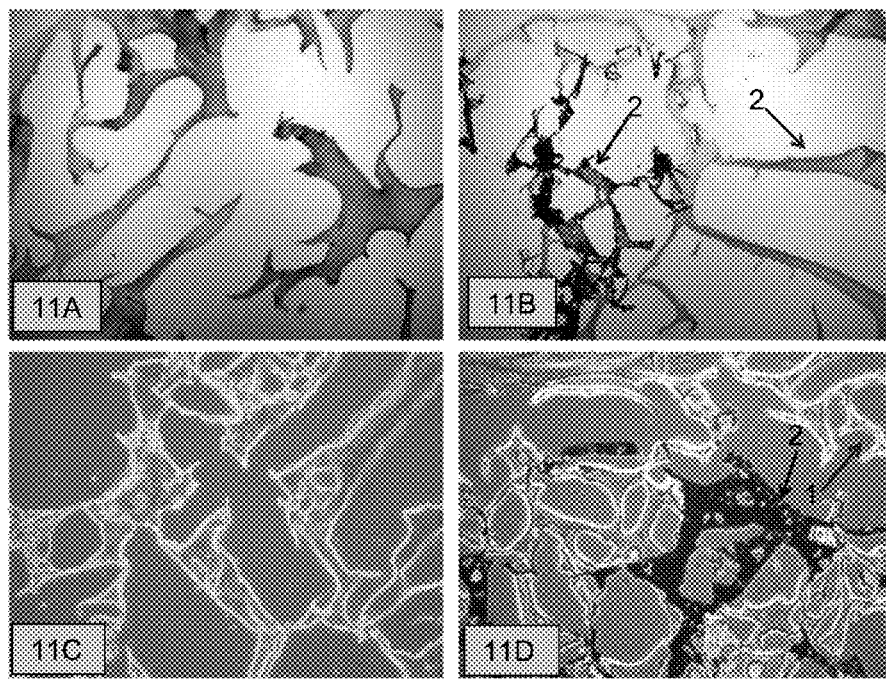
FIGS. 11A-11D illustrates results of safranin-O staining for GAGs in the cartilage phase (FIG. 11A), the interface of the bone and cartilage phases (FIG. 11B), acellular agarose control (FIG. 11C), and the interface of the acellular control (FIG. 11D). Original total magnification of all micrographs was 50×.

The results of safranin-O staining for glycosaminoglycans are shown in FIGS. 11A-11D including the cartilage phase (FIG. 11A), the interface of the bone and cartilage phases (FIG. 11B), acellular agarose control (FIG. 11C), and the interface of the acellular control (FIG. 11D). The cartilage phase (FIG. 11A) showed strong red-orange staining indicating the presence of GAGs throughout the entire phase. The red-orange staining was present in the agarose through the entire cartilage phase and was not present in the bone phase (FIG. 11B). Arrow 1 indicates cartilage phase and arrows 2 indicate bone phase.

Figure 12:
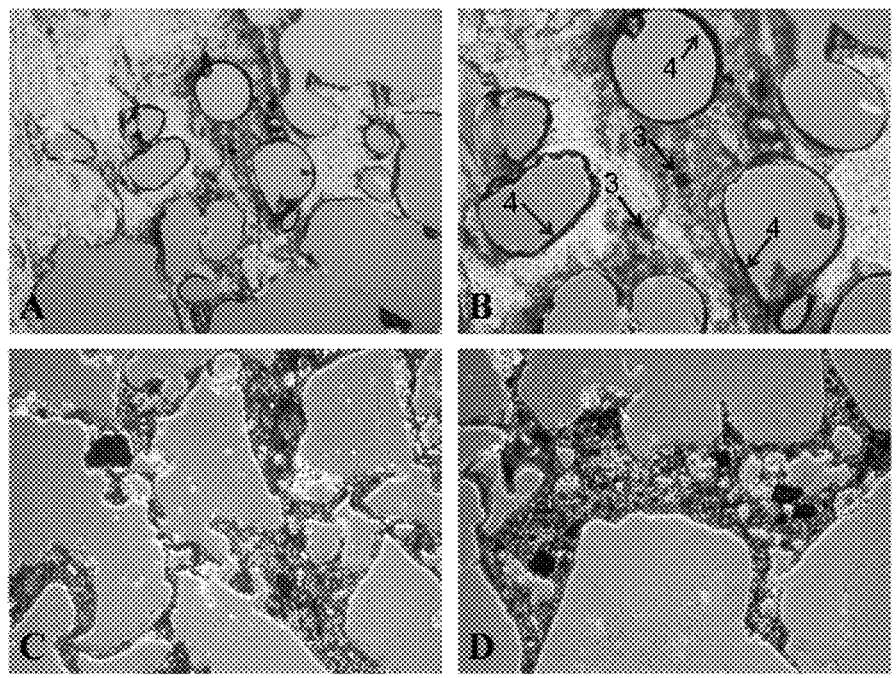
FIG. 12 illustrates results of the Dahl's staining method for mineralization in the bone phase at 50× original total magnification (FIG. 12A) and 100× original total magnification (FIG. 12B) and the acellular control at 50× (FIG. 12C) and 100× (FIG. 12D).

The results of Dahl's staining method for calcium to visualize the presence of mineralization are shown in FIGS. 12A-12D at 50× original total magnification (FIG. 12A) and 100× original total magnification (FIG. 12B) and the acellular control at 50× (FIG. 12C) and 100× (FIG. 12D). The HAP particles that are part of the scaffold 3 were stained red throughout the PL/PCL matrix. Red staining indicated that mineralization only occurred along the edges of the pores of the scaffolds cultured in the bioreactor. Arrows 4 indicate mineralization generated by the cells.

Figure 13:
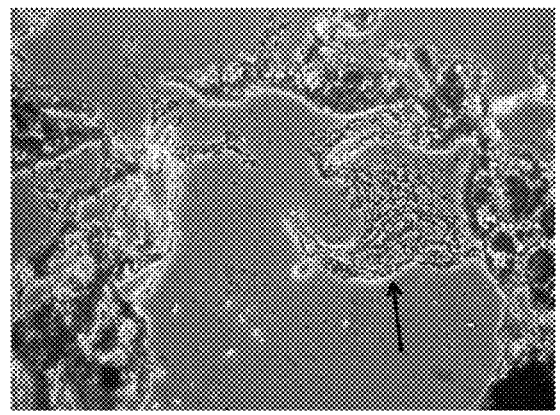
FIG. 13 illustrates results of the Masson's trichrome staining. Original total magnification was 200×.

The results of the Masson's trichrome stain are shown in FIG. 13. The presence of collagen is indicated by blue staining and the arrow. Collagen fibers were attached to the PL/PCL/HAP scaffolds and extended into the pores of the structure.

Figure 14:
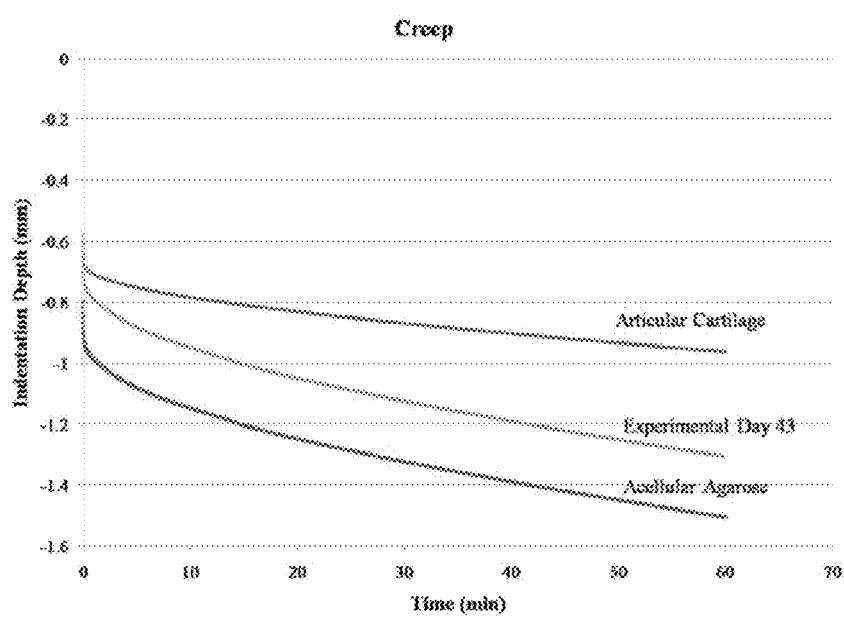
FIG. 14 illustrates typical creep profiles of the acellular agarose controls, articular cartilage, and the experimental samples.

The typical results of the indentation creep test are show in FIG. 14. The initial indentation due to the 1 N load and total creep over the 60 minute test are shown in Table 1, below.

TABLE 1

| Sample | Initial Indentation (mm) | Total Creep (mm) |
|---|---|---|
| Acellular agarose control | 0.95 ± 0.22 | 0.6 ± 0.17 |
| Articular cartilage | 0.68 ± 0.18 | 0.31 ± 0.12 |
| Experimental sample | 0.77 ± 0.23 | 0.51 ± 0.20 |

The initial indentation decreased from 0.95±0.22 mm in the acellular agarose controls to 0.77±0.23 mm in the constructs cultured in the bioreactor. The initial indentation of articular cartilage was 0.68±0.18 mm. The total creep decreased from 0.60±0.17 mm in the acellular agarose controls to 0.51±0.20 mm in the constructs cultured in the bioreactor. The total creep in the articular cartilage was 0.31±0.12.

Figure 15:
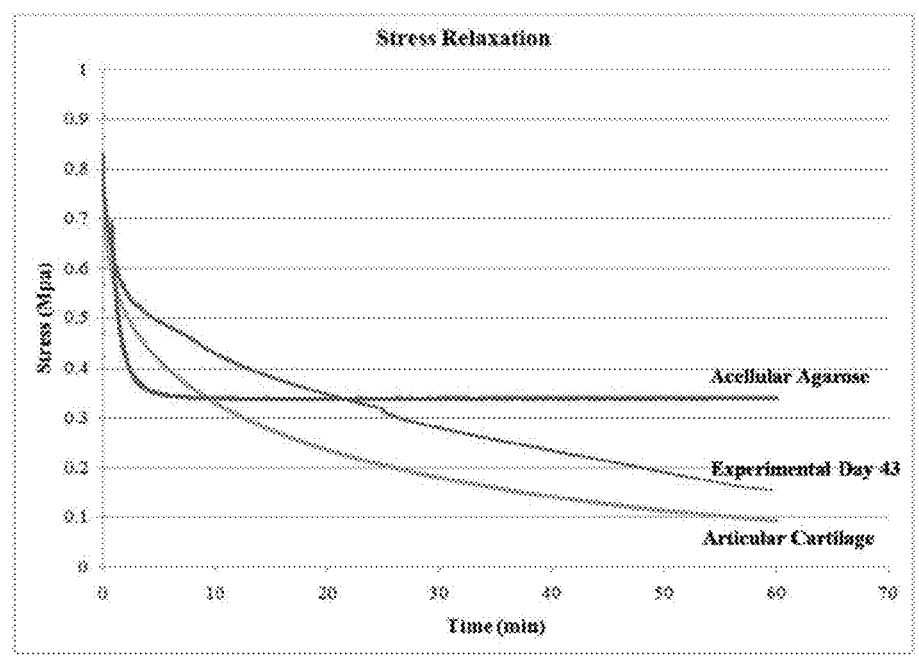
FIG. 15 illustrates typical stress relaxation profiles of the acellular agarose controls, articular cartilage, and the experimental samples.

The typical results of the stress relaxation test are show in FIG. 15. The initial stress required for the initial 3% strain and the total stress relaxation over the 60 minute test are shown in Table 2, below.

TABLE 2

| Acellular agarose control | Initial Stress (kPa) | Total Relaxation (kPa) |
|---|---|---|
| Acellular agarose control | 680 ± 180 | 370 ± 130 |
| Articular cartilage | 1330 ± 270 | 1190 ± 320 |
| Experimental sample | 820 ± 290 | 630 ± 240 |

The initial stress increased from 680±180 kPa in the acellular agarose controls to 820±290 mm in the constructs cultured in the bioreactor. The initial stress of articular cartilage was 1330±270 kPa. The total relaxation increased from 370±130 kPa in the acellular agarose controls to 630±240 mm in the constructs cultured in the bioreactor. The total stress relaxation in the articular cartilage was 1190±320.

EXAMPLE 3

An osteochondral construct as illustrated in FIG. 5 was formed. Initially, the large fiber bundle that makes up the bone portion of the construct was formed. Tecoflex™, a thermoplastic polyurethane, was extruded trough a specially designed die to create the unique geometry of the wicking fibers. The fibers were cut into lengths of approximately 10 mm. A group of four fibers were placed together. To form a bundle, the four fibers were simultaneously stretched and twisted. Four bundles were then used to form a larger bundle using the same stretching and twisting technique. This resulted in one large bundle composed of four bundles of four fibers.

Following formation of the fiber bundle, a PCL/PLA ring was formed to function as an anchor. A small rod of PCL/PLA was formed using compression molding techniques as described above. The rod was then formed in to a circle by heating the ends and holding them together and allowing the polymer to solidify. The large fiber bundle was then inserted into the ring and the area where the bundle and ring contacted was heated allowing for the polymers to melt and attach to one another.

A small porous section of polymer was formed to attach the hydrogel of the cartilage portion to the rest of the construct. A layer of porous PLA/PCL was formed using the solvent casting/particle leaching method as previously described, and the bottom of the porous layer was heated and pressed to the anchor ring surrounding the fiber bundle.

Finally, the hydrogel of the cartilage portion was formed on this porous polymer section. 2% agarose was sterilized in an autoclave, which also dissolved the agarose. The agarose was brought back down to 32° C. A cell suspension of mesenchymal stem cells was added to the agarose and mixed to create a uniform distribution of cells. The cell/agarose mixture was placed in a cylindrical mold with a diameter of 7 mm. The remainder of the construct that was previously formed was inserted in the mold and extended into the agarose approximately 2 mm. The agarose penetrated into the porous scaffold and provided attachment between the two portions. The construct was placed at 2° C. for 10 minutes to allow the agarose to gel.

Following, the bone portion of the construct can be seeded with mesenchymal stem cells.

It will be appreciated that the foregoing examples, given for purposes of illustration, are not to be construed as limiting the scope of this disclosure. Although only a few exemplary embodiments of the disclosed subject matter have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. An osteochondral construct comprising:
   a cartilage portion, the cartilage portion including a hydrogel comprising a polymeric matrix;
   a bone portion comprising at least one capillary channeled fiber, the capillary channeled fiber having a non-circular cross section and including a plurality of co-linear channels extending the entire length of the exterior surface of the capillary channeled fiber, the capillary channeled fiber defining a fluid conduit within the bone portion, the bone portion being adjacent to the cartilage portion; and
   a polymeric anchor adjacent to at least one of the bone portion and the cartilage portion, the polymeric anchor providing a pressure fit between the osteochondral construct and a surrounding structure.

2. The osteochondral construct of claim 1, the bone portion further comprising a polymer/ceramic composite material including a biocompatible polymer and a calcium phosphate ceramic.

3. The osteochondral construct of claim 2, wherein the calcium phosphate ceramic comprises at least one of hydroxyapatite and tricalcium phosphate.

4. The osteochondral construct of claim 2, the polymer/ceramic composite material comprising a polylactide copolymer.

5. The osteochondral construct of claim 1, the bone portion comprising multiple capillary channeled fibers, the bone portion defining a fluid conduit between adjacent capillary channeled fibers.

6. The osteochondral construct of claim 1, the bone portion being between the cartilage portion and the polymeric anchor.

7. The osteochondral construct of claim 1, wherein the polymeric anchor encircles a portion of the cartilage portion or the bone portion.

8. The osteochondral construct of claim 1, the bone portion comprising a bundle of capillary channeled fibers.

9. The osteochondral construct of claim 1, the bone portion comprising a plurality of bundles of capillary channeled fibers.

10. The osteochondral construct of claim 1, the polymeric matrix of the hydrogel comprising a hydrolyzable portion.

11. The osteochondral construct of claim 1, at least one of the cartilage portion and the bone portion comprising a cell.

12. The osteochondral construct of claim 11, wherein the cartilage portion comprises a cell and the cell is a chondrocyte or an undifferentiated mesenchymal stem cell.

13. The osteochondral construct of claim 11, wherein the bone portion comprises a cell and the cell is an osteoblast or an osteocyte.

14. The osteochondral construct of claim 1, wherein at least one of the bone portion, the cartilage portion, and the polymeric anchor further comprises a bioactive agent.

15. The osteochondral construct of claim 1, wherein the polymeric anchor comprises a polymer having a glass transition temperature of less than about 37° C.

* * * * *